(12) United States Patent
Higgins et al.

(10) Patent No.: US 11,202,900 B2
(45) Date of Patent: Dec. 21, 2021

(54) INTRAVASCULAR PUMP WITH CONTROLS AND DISPLAY SCREEN ON HANDLE

(71) Applicant: Cardiovascular Systems, Inc., St. Paul, MN (US)

(72) Inventors: Joseph P. Higgins, Minnetonka, MN (US); Matthew W. Tilstra, Rogers, MN (US); Benjamin D. Haselman, St. Paul, MN (US); Matthew D. Cambronne, North Oaks, MN (US); Tristan A. Van de Moortele, Minneapolis, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 324 days.

(21) Appl. No.: 16/524,791

(22) Filed: Jul. 29, 2019

(65) Prior Publication Data
US 2020/0038568 A1    Feb. 6, 2020

Related U.S. Application Data

(60) Provisional application No. 62/712,409, filed on Jul. 31, 2018.

(51) Int. Cl.
*A61M 1/10*     (2006.01)
*A61M 60/50*    (2021.01)
(Continued)

(52) U.S. Cl.
CPC .......... *A61M 60/50* (2021.01); *A61M 60/148* (2021.01); *A61M 60/205* (2021.01);
(Continued)

(58) Field of Classification Search
CPC .......... A61M 60/148; A61M 2205/502; A61M 2205/50; A61M 60/122; A61M 60/205;
(Continued)

(56) References Cited

U.S. PATENT DOCUMENTS

| 7,699,586 B2 | 4/2010 | Larose et al. |
| 2004/0191116 A1 | 9/2004 | Jarvik et al. |

(Continued)

FOREIGN PATENT DOCUMENTS

| EP | 1996252 | 5/2016 |
| WO | 2018073150 | 4/2018 |

OTHER PUBLICATIONS

International Preliminary Report on Patentability, dated Feb. 11, 2021 in PCT Application No. PCT/US19/44040, filed Jul. 30, 2019.

(Continued)

*Primary Examiner* — Jon Eric C Morales
(74) *Attorney, Agent, or Firm* — Barnes & Thornbugr LLP; Jeffrey R. Stone

(57) ABSTRACT

The present invention provides an intravascular blood pump comprising a handle in operational connection and communication with a rotational motor and impeller assembly that is configured for placement and positioning within a patient's vasculature. The handle comprises a display for displaying real-time physiological parameters associated with the blood pump procedure and controls for modifying operational parameters. In some embodiments, the display portion of the handle may be connected and/or disconnected from the non-display portion to allow re-use of the display portion in subsequent blood pump procedures.

20 Claims, 6 Drawing Sheets

(51) Int. Cl.
  *A61M 60/148* (2021.01)
  *A61M 60/205* (2021.01)
  *A61M 60/422* (2021.01)

(52) U.S. Cl.
  CPC ... *A61M 60/422* (2021.01); *A61M 2205/3334* (2013.01); *A61M 2205/3344* (2013.01); *A61M 2205/3365* (2013.01); *A61M 2205/502* (2013.01); *A61M 2230/04* (2013.01); *A61M 2230/06* (2013.01); *A61M 2230/20* (2013.01); *A61M 2230/30* (2013.01)

(58) Field of Classification Search
  CPC .... A61M 60/50; A61M 60/40; A61N 1/37235
  See application file for complete search history.

(56) References Cited

U.S. PATENT DOCUMENTS

| | | |
|---|---|---|
| 2009/0067989 A1 | 3/2009 | Estes et al. |
| 2010/0222634 A1 | 9/2010 | Poirier |
| 2014/0365691 A1 | 12/2014 | Schoenle et al. |

OTHER PUBLICATIONS

International Search Report and Written Opinion, dated Oct. 21, 2019 for PCT Application No. PCT/US19/44040, filed Jul. 30, 2019.

INTRAVASCULAR PUMP WITH CONTROLS AND DISPLAY SCREEN ON HANDLE

CROSS-REFERENCE TO RELATED APPLICATIONS

This application claims priority to U.S. Provisional Patent Application No. 62/712,409, filed Jul. 31, 2018 and titled INTRAVASCULAR PUMP WITH CONTROLS AND DISPLAY SCREEN ON HANDLE, the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with controls and display screen on the handle.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a flow inducer, known in the art as component that directs flow into the impeller from the inflow apertures or inlet; a rotational impeller; and a flow diffuser and/or outflow structure known in the art as functioning to straighten or redirecting the rotational flow created by the rotational impeller into axial flow; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the flow inducer 6 before being urged forward by the rotating impeller 8. The blood flow may then be modified by a flow diffuser 9 and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 3:
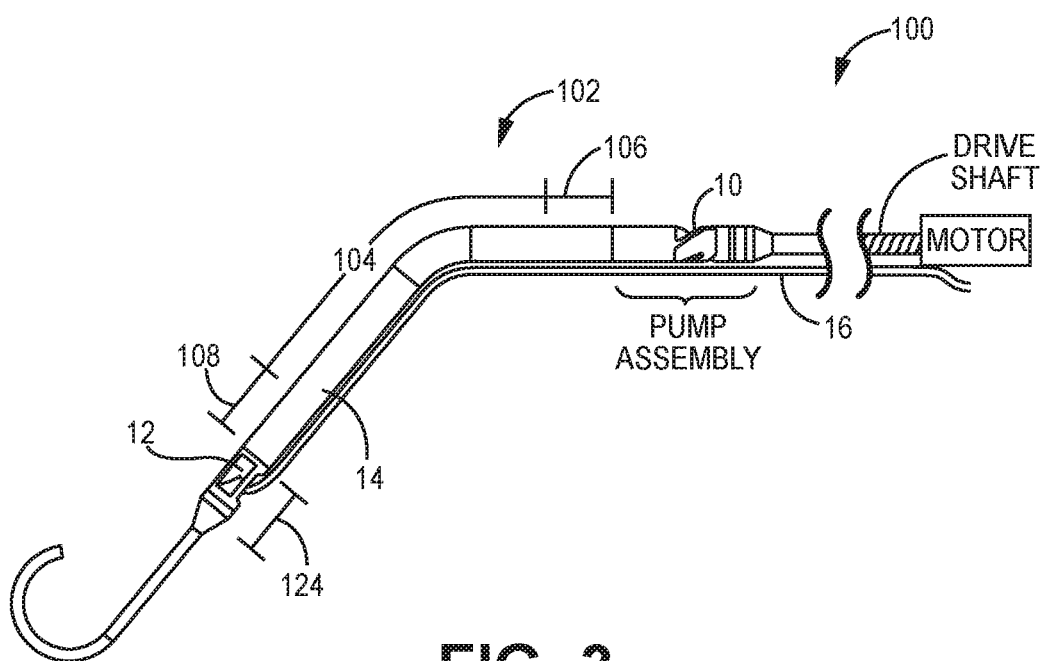
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
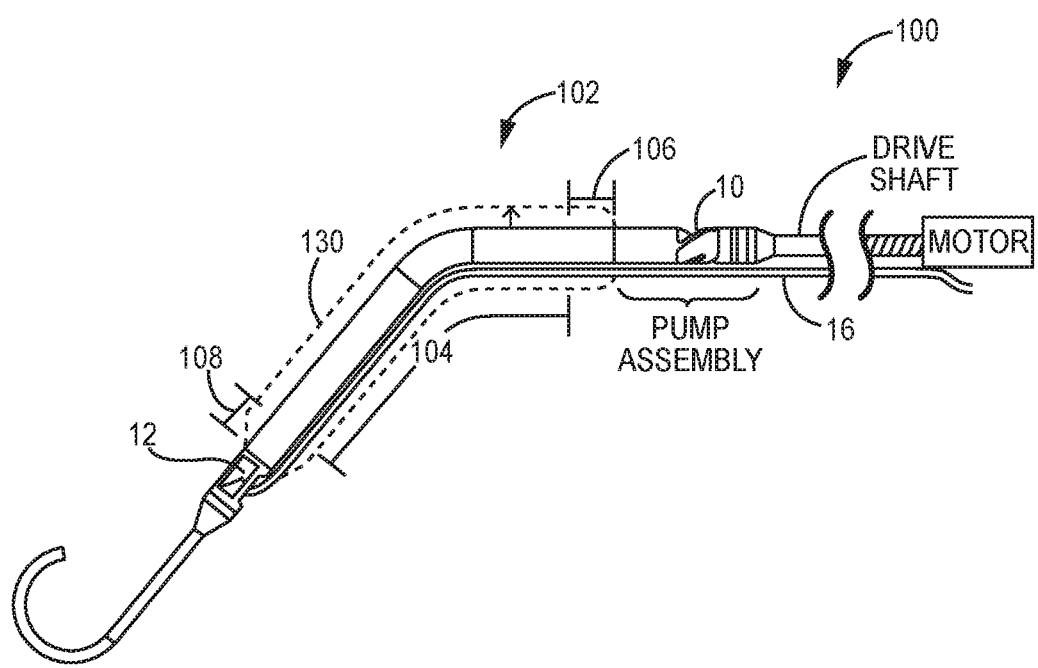
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing. Expandable region 102 may also comprise a single region capable of expansion and collapse.

Figure 1:
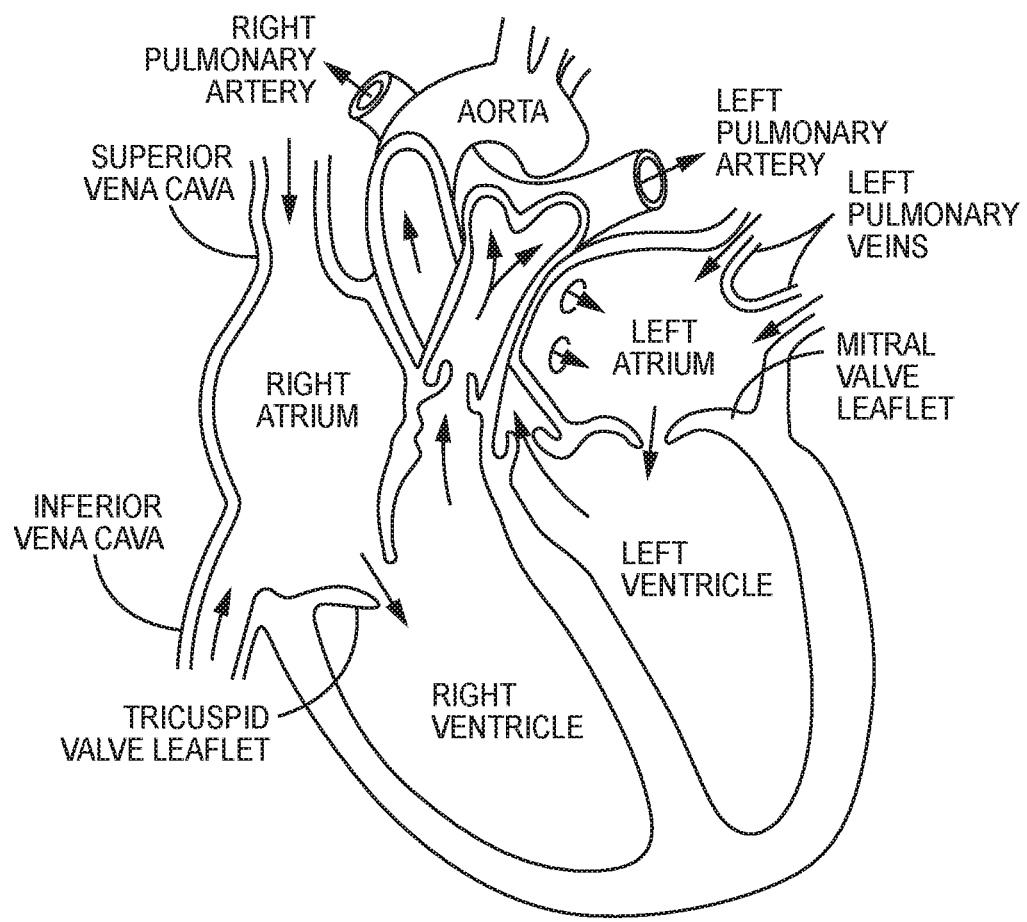
FIG. 1 is a cutaway view of the human heart.
Figure 2:
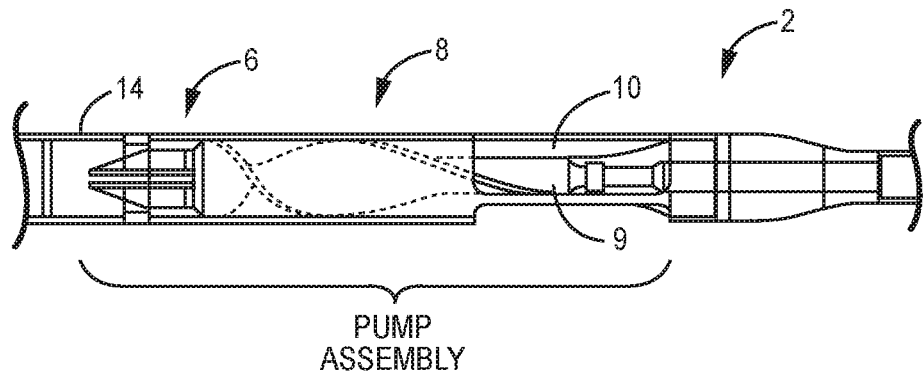
FIG. 2 is a cross-sectional view of a prior art device.
Figure 5:
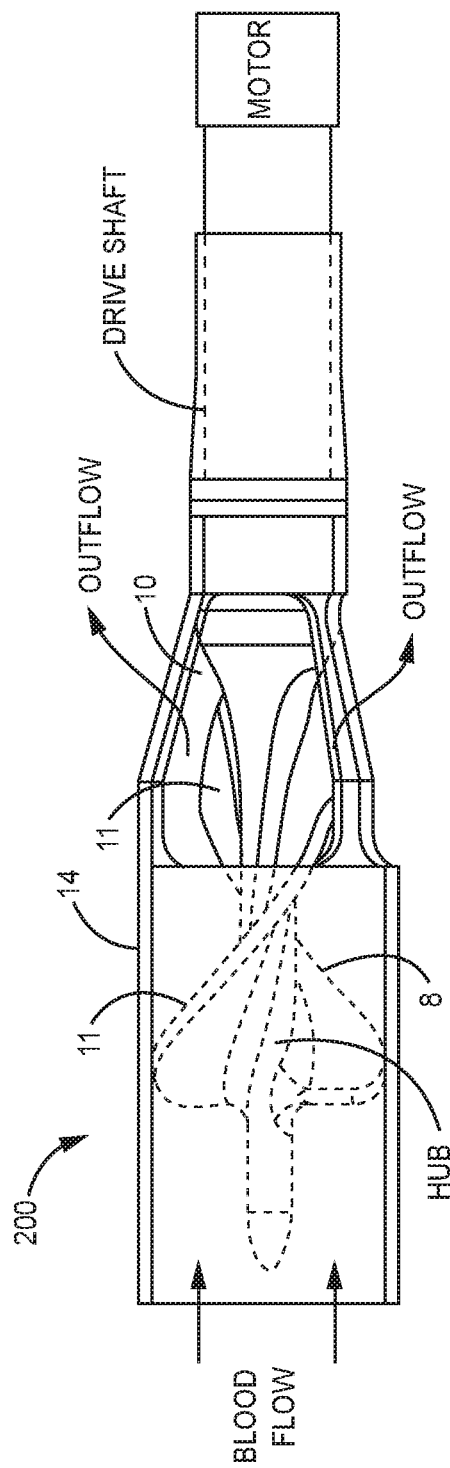
FIG. 5 is a side cutaway of one embodiment of the present invention.

Turning now to FIG. 5, an exemplary pump assembly or impeller assembly 200 is illustrated. Initially, in contrast to the known impeller assembly shown in FIG. 2 which comprises a flow inducer 6 and flow diffuser 9, the exemplary pump or impeller assembly of FIG. 5 completely eliminates the flow inducer 6 and the flow diffuser 9 of the impeller assembly found in known pumps. Applicant has found that the inducer 6 and/or diffuser 9 are not needed for effective control or manipulation of the incoming blood flow and that the additional stationary surface area and interconnections between at least the inducer 6 and the distal end of the rotating impeller 8 provide increased risk of thrombosis. Thus, the blood is induced to flow through the cannula of by actuating the pump or impeller assembly to rotate at a predetermined speed, without aid or requirement of a flow inducer. The blood thus flows directly to the rotating impeller 8 comprising blades 11 and is urged out of the cannula or lumen of the device at outlet apertures 10 by the rotating impeller blades 11, without aid or requirement of a flow diffuser or straightener.

Turning now to FIGS. 6-8B, embodiments of a blood pump assembly comprising a handle with control buttons and a display on the handle are provided. In some cases, a rotational motor may be provided in operational engagement with the impeller assembly and may be disposed within the device and within the patient's vasculature. In other embodiments, an external rotational motor may be provided in operational engagement with a drive shaft that is, in turn, operationally engaged with the impeller assembly.

Generally, a blood pump assembly of the present invention may comprise:

a motor in operative rotational engagement with an impeller assembly, the impeller assembly comprising an impeller housing, an impeller within the impeller housing, the impeller comprising an impeller hub and blades in operative engagement with the impeller hub; and a handle in operative connection and communication with the motor, wherein the handle comprises controls for controlling at least the motor, and a display integrated into the handle, the display adapted to display real-time physiological parameters and operational parameters, wherein the real-time physiological parameters comprise at least one of the group consisting of: blood pressure, heart rate, electrocardiogram information, and blood oxygen saturation, and wherein the real-time operational parameters comprise at least one of the group consisting of: rotational speed, resulting blood flow rate induced by the blood pump within the patient's vasculature, and resulting blood pressure induced by the blood pump within the patient's vasculature.

In some cases, the impeller assembly and/or impeller may comprise a flow inducer and/or flow straightener, while in other embodiments no flow inducer or flow straightener is required. Further, as described herein, the motor may be integrated within the device and inserted within the patient's vasculature with the device. In other cases, the motor may be disposed within the handle with a rotational drive shaft disposed within the sheath and in operative engagement with the rotational motor and the impeller assembly.

Figure 6:
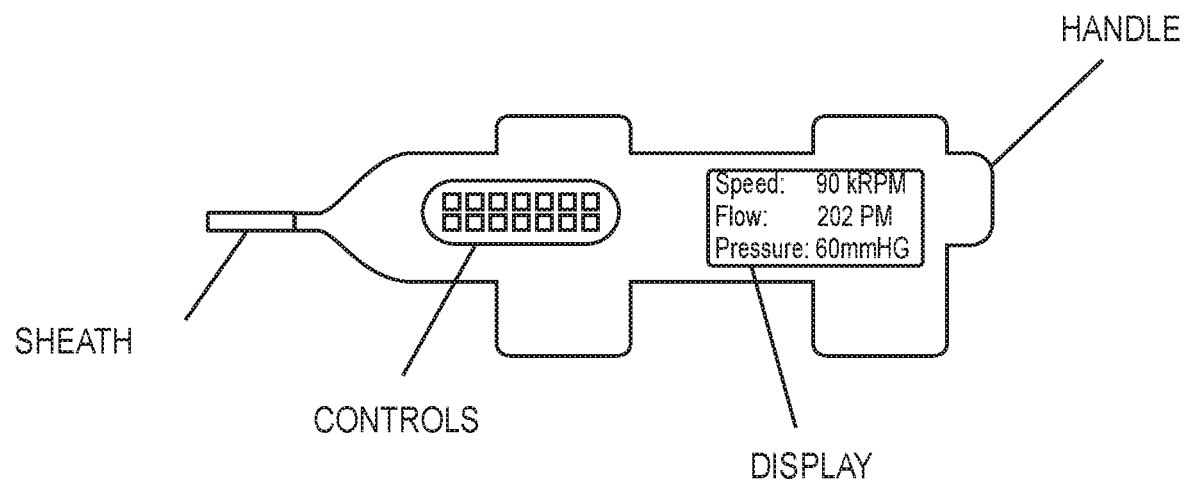
FIG. 6 is a top view cutaway view of a handle of one embodiment of the present invention.

FIG. 6 shows the physiological parameters on a display with controls for controlling the operational parameters that may be adjusted according to the displayed physiological parameters being or trending high or low compared with desired physiological parameter targets.

Figure 7:
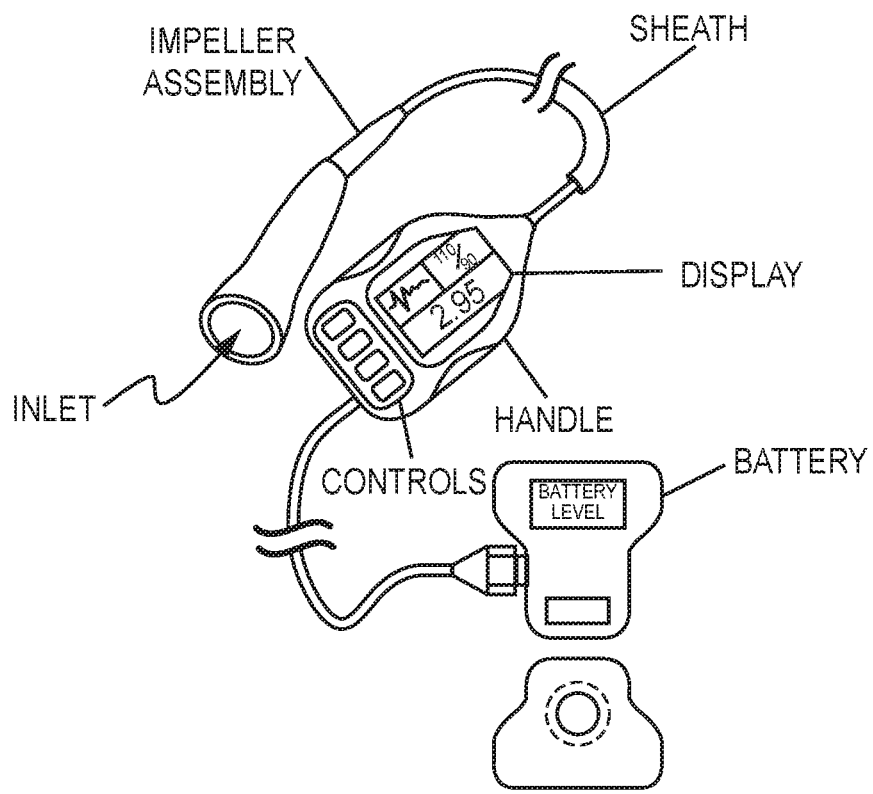
FIG. 7 is a perspective view of one embodiment of the present invention.

FIG. 7 shows one embodiment of the handle in operative connection with an impeller assembly and any physiological sensors along the sheath and/or in or proximate to the impeller assembly. As will be readily understood, electrical leads may be translated through the sheath to operatively connect the handle with a motor and/or impeller assembly and/or physiological parameter sensors or operational sensors such as pressure of flow or flow rate generated or induced by the rotating impeller.

Figure 8A:
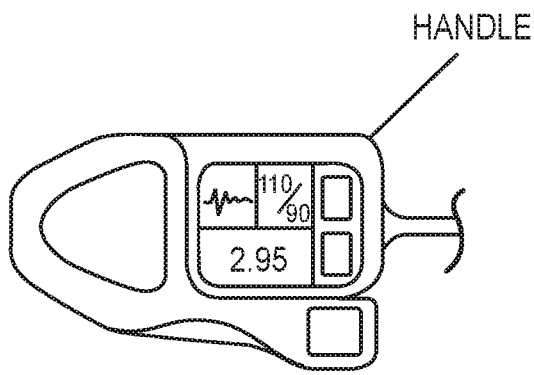
FIG. 8A is a top view of a handle with a display portion connected with a non-display portion.
Figure 8B:
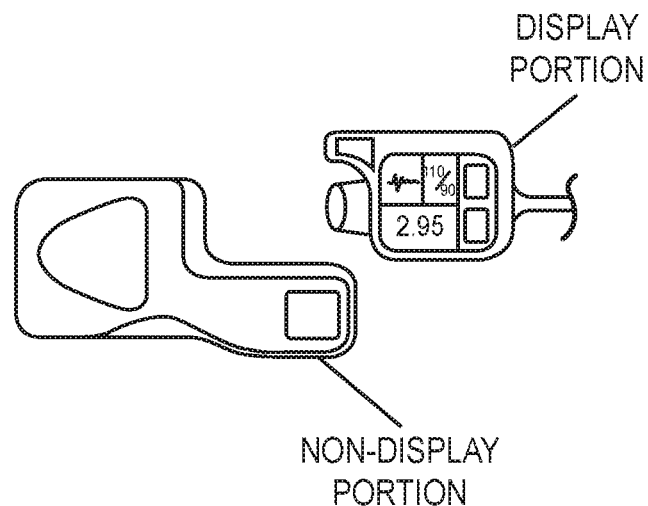
FIG. 8B is a top view of the handle of FIG. 8A wherein the display portion is disconnected from the non-display portion.

FIGS. 8A and 8B illustrate one embodiment wherein the handle comprises a reusable display portion and a non-reusable non-display portion. The display portion may be removably connected with and to the non-display portion to enable operative functioning and monitoring as described above. When a blood pump procedure is completed, the display portion may be disconnected and reused with another non-display portion and in another blood pump procedure.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump assembly adapted for use within a patient's vasculature, comprising:
    a motor in operative rotational engagement with an impeller assembly, the impeller assembly comprising an impeller housing, an impeller within the impeller housing, the impeller comprising an impeller hub and blades in operative engagement with the impeller hub; and
    a handle in operative connection and communication with the motor, wherein the handle comprises controls for controlling at least the motor, and a display integrated into the handle, the display adapted to display real-time physiological parameters and operational parameters, wherein the real-time physiological parameters comprise at least one of the group consisting of: blood pressure, heart rate, electrocardiogram information, and blood oxygen saturation, and
    wherein the real-time operational parameters comprise at least one of the group consisting of: rotational speed, resulting blood flow rate induced by the blood pump within the patient's vasculature, and resulting blood pressure induced by the blood pump within the patient's vasculature.

2. The blood pump assembly of claim 1, further comprising a drive shaft in operational rotational engagement with the impeller assembly and the motor, wherein the motor is located within the handle and outside of the patient's vasculature.

3. The blood pump assembly of claim 1, wherein the motor is located within the patient's vasculature.

4. The blood pump assembly of claim 1, wherein the handle comprises a display portion and a non-display portion, wherein the display portion is adapted to be operatively and removably connected with the non-display portion.

5. The blood pump assembly of claim 4, wherein the display portion is adapted for re-use after completing a procedure within the patient's vasculature after disconnecting the re-usable display portion from the used non-display portion.

6. The blood pump assembly of claim 1, wherein the impeller assembly does not include a flow inducer or a flow diffuser.

7. A blood pump assembly adapted for use within a patient's vasculature, comprising:
    a motor in operative rotational engagement with an impeller assembly, the impeller assembly comprising an impeller housing, an impeller within the impeller housing,
    the impeller comprising an impeller hub and blades in operative engagement with the impeller hub; and
    a handle in operative connection and communication with the motor, wherein the handle comprises controls for controlling at least the motor, and a display integrated into the handle, the display adapted to display real-time physiological parameters and real-time operational parameters,
    wherein the handle comprises a display portion and a non-display portion, wherein the display portion is adapted to be operatively and removably connected with the non-display portion.

8. The blood pump assembly of claim 7, wherein the display portion is adapted for re-use after completing a procedure within the patient's vasculature and after disconnecting the re-usable display portion from the used non-display portion.

9. The blood pump assembly of claim 7, wherein the real-time physiological parameters comprise at least one of the group consisting of: blood pressure, heart rate, electrocardiogram information, and blood oxygen saturation.

10. The blood pump assembly of claim 7, wherein the real-time operational parameters comprise at least one of the group consisting of: rotational speed, resulting blood flow rate induced by the blood pump within the patient's vasculature, and resulting blood pressure induced by the blood pump within the patient's vasculature.

11. The blood pump assembly of claim 7, further comprising a drive shaft in operational rotational engagement with the impeller assembly and the motor, wherein the motor is an external motor located proximal to the impeller assembly and outside of the patient's vasculature.

12. The blood pump assembly of claim 11, wherein the motor is located within the handle.

13. The blood pump assembly of claim 7, wherein the motor is located within the patient's vasculature.

14. A blood pump assembly adapted for use within a patient's vasculature, comprising:
    a motor in operative rotational engagement with an impeller assembly, the impeller assembly comprising an impeller housing, an impeller within the impeller housing, the impeller comprising an impeller hub and blades in operative engagement with the impeller hub, wherein the impeller assembly does not include a flow inducer or a flow diffuser; and
    a handle in operative connection and communication with the motor, wherein the handle comprises controls for controlling at least the motor, and a display integrated into the handle, the display adapted to display real-time physiological parameters and real-time operational parameters.

15. The blood pump assembly of claim 14, wherein the real-time physiological parameters comprise at least one of the group consisting of: blood pressure, heart rate, electrocardiogram information, and blood oxygen saturation.

16. The blood pump assembly of claim 14, wherein the real-time operational parameters comprise at least one of the group consisting of: rotational speed, resulting blood flow rate induced by the blood pump within the patient's vasculature, and resulting blood pressure induced by the blood pump within the patient's vasculature.

17. The blood pump assembly of claim 14, further comprising a drive shaft in operational rotational engagement with the impeller assembly and the motor, wherein the motor is an external motor located proximal to the impeller assembly and outside of the patient's vasculature.

18. The blood pump assembly of claim 14, wherein the motor is located within the patient's vasculature.

19. The blood pump assembly of claim 13, wherein the handle comprises a display portion and a non-display portion, wherein the display portion is adapted to be operatively and removably connected with the non-display portion.

20. The blood pump assembly of claim 19, wherein the display portion is adapted for re-use after completing a procedure within the patient's vasculature after disconnecting the re-usable display portion from the used non-display portion.

* * * * *